United States Patent
Dave et al.

(10) Patent No.: US 10,520,372 B2
(45) Date of Patent: Dec. 31, 2019

(54) OPTICAL MANUFACTURING PROCESS SENSING AND STATUS INDICATION SYSTEM

(71) Applicant: SIGMA LABS, INC., Santa Fe, NM (US)

(72) Inventors: Vivek R. Dave, Concord, NH (US); Mark J. Cola, Santa Fe, NM (US); R. Bruce Madigan, Butte, MT (US); Martin S. Piltch, Los Alamos, NM (US); Alberto Castro, Santa Fe, NM (US)

(73) Assignee: SIGMA LABS, INC., Santa Fe, NM (US)

( * ) Notice: Subject to any disclaimer, the term of this patent is extended or adjusted under 35 U.S.C. 154(b) by 0 days.

(21) Appl. No.: 16/434,577

(22) Filed: Jun. 7, 2019

(65) Prior Publication Data
US 2019/0323903 A1    Oct. 24, 2019

Related U.S. Application Data

(63) Continuation of application No. 15/276,452, filed on Sep. 26, 2016, now Pat. No. 10,317,294, which is a
(Continued)

(51) Int. Cl.
*G01J 3/30*    (2006.01)
*G01K 13/00*   (2006.01)
(Continued)

(52) U.S. Cl.
CPC ............ *G01K 13/00* (2013.01); *B22F 3/1055* (2013.01); *B23K 9/04* (2013.01); *B23K 9/095* (2013.01);
(Continued)

(58) Field of Classification Search
CPC ........ G01J 3/4406; G01J 3/02; G01N 21/718; G01N 21/645; G01N 21/6458
(Continued)

(56) References Cited

U.S. PATENT DOCUMENTS 6,461,035 B2   10/2002   Meinlschmidt et al.
6,616,332 B1    9/2003   Renken et al.
(Continued)

FOREIGN PATENT DOCUMENTS

EP      1967857 A2       9/2008
WO      2015148702      10/2015
WO      2015148702 A8   11/2015

OTHER PUBLICATIONS

U.S. Appl. No. 15/276,452, "Non-Final Office Action", dated Apr. 6, 2018, 20 pages.
(Continued)

*Primary Examiner* — Md M Rahman
(74) *Attorney, Agent, or Firm* — Kilpatrick Townsend & Stockton LLP

(57) ABSTRACT

An optical manufacturing process sensing and status indication system is taught that is able to utilize optical emissions from a manufacturing process to infer the state of the process. In one case, it is able to use these optical emissions to distinguish thermal phenomena on two timescales and to perform feature extraction and classification so that nominal process conditions may be uniquely distinguished from off-nominal process conditions at a given instant in time or over a sequential series of instants in time occurring over the duration of the manufacturing process. In other case, it is able to utilize these optical emissions to derive corresponding spectra and identify features within those spectra so that nominal process conditions may be uniquely distinguished from off-nominal process conditions at a given instant in
(Continued)

time or over a sequential series of instants in time occurring over the duration of the manufacturing process.

20 Claims, 4 Drawing Sheets

Related U.S. Application Data continuation of application No. PCT/US2015/022539, filed on Mar. 25, 2015.

(60) Provisional application No. 61/970,407, filed on Mar. 26, 2014.

(51) Int. Cl.
| | |
|---|---|
| *G01N 21/71* | (2006.01) |
| *G01J 3/28* | (2006.01) |
| *G01J 3/443* | (2006.01) |
| *B33Y 10/00* | (2015.01) |
| *B33Y 30/00* | (2015.01) |
| *B33Y 50/00* | (2015.01) |
| *B23K 26/342* | (2014.01) |
| *B23K 26/70* | (2014.01) |
| *B22F 3/105* | (2006.01) |
| *B23K 9/04* | (2006.01) |
| *B23K 9/095* | (2006.01) |
| *B23K 10/02* | (2006.01) |
| *B23K 15/00* | (2006.01) |

(52) U.S. Cl.
CPC .......... *B23K 9/0953* (2013.01); *B23K 9/0956* (2013.01); *B23K 10/027* (2013.01); *B23K 15/0026* (2013.01); *B23K 15/0086* (2013.01); *B23K 26/342* (2015.10); *B23K 26/70* (2015.10); *B33Y 10/00* (2014.12); *B33Y 30/00* (2014.12); *B33Y 50/00* (2014.12); *G01J 3/28* (2013.01); *G01J 3/2889* (2013.01); *G01J 3/443* (2013.01); *G01N 21/71* (2013.01); *B22F 2003/1057* (2013.01)

(58) Field of Classification Search
USPC ........................................................ 356/318
See application file for complete search history.

(56) References Cited

U.S. PATENT DOCUMENTS

| | | |
|---|---|---|
| 7,744,274 B1 | 6/2010 | Grek et al. |
| 2005/0018744 A1 | 1/2005 | Schonlein et al. |
| 2008/0228306 A1 | 9/2008 | Yetter et al. |
| 2011/0155043 A1 | 6/2011 | Haarer et al. |
| 2013/0114082 A1 | 5/2013 | Sailor et al. |
| 2014/0022546 A1 | 1/2014 | Nagai et al. |
| 2017/0016781 A1 | 1/2017 | Dave et al. |

OTHER PUBLICATIONS

U.S. Appl. No. 15/276,452, "Notice of Allowance", dated Jan. 25, 2019, 13 pages.
PCT/US2015/022539, "International Preliminary Report on Patentability", dated Oct. 6, 2016, 8 pages.
PCT/US2015/022539, "International Search Report and Written Opinion", dated Jun. 23, 2015, 8 pages.

OPTICAL MANUFACTURING PROCESS SENSING AND STATUS INDICATION SYSTEM

CROSS-REFERENCES TO RELATED APPLICATIONS

This application is a continuation of U.S. patent application Ser. No. 15/276,452, filed Sep. 26, 2016; which is a continuation of and claims priority to PCT/US2015/022539, filed Mar. 25, 2015; which claims the benefit of U.S. Provisional Patent Application No. 61/970,407, filed Mar. 26, 2014. The disclosures of each are hereby incorporated by reference in their entirety for all purposes.

DESCRIPTION OF INVENTION

For manufacturing processes that involve the addition of heat at relatively fast timescales and the removal of heat through conduction and other mechanisms such as convection and radiation at relatively slower timescales, it is desirable to have a process sensing and process status indication system that can independently and separately compare if the heat input as well as the material response is largely similar or very different between two different processing conditions. For processes that get relatively hot, i.e. above 700 C, there is observable optical radiation from the process which can serve as the basis of a sensing mechanism. This can form the basis of an in-process quality assurance methodology that can use the in-process data from both the faster heat input processes as well as the slower heat dissipation processes to determine if a given process condition is largely similar to the desired baseline process condition, or if it is very different from this desired baseline process condition.

Embodiments of the present invention can enable an optical sensing system to identify, examine, and analyze features associated with a heat source from two different process conditions and determine if they are largely similar or very different. Embodiments of the present invention can also identify, examine, and analyze features associated with the material response to a heat input associated with two different process conditions to determine if they are largely similar or very different. Embodiments of the present invention can also determine if the features from the faster timescale heat input and associated with a given process condition are largely similar to those associated with a known baseline process condition and therefore considered nominal or very different from that baseline condition and therefore considered off-nominal. Embodiments of the present invention can determine if process features from the slower material response to the heat input and associated with a given process condition are largely similar to those associated with a known baseline process condition and therefore considered nominal or very different from that baseline condition and therefore considered off-nominal.

There are many examples of manufacturing processes involving the addition of heat on a relatively rapid timescale and the response of the material over a relatively slower timescale. For example, consider the autogenous welding of a part (i.e. no addition of material) comprising a scanning heat source moving rapidly over the joint between the two metal surfaces to be joined. Assume that the diameter of the heat source is D and the travel speed of the heat source is V. Therefore, the characteristic time of interaction between the heat source and the pieces of metal to be joined is described by the following equation:

$$t_{heat\ source} = \frac{D}{V} \quad (1)$$

It is seen that for very small D and very large V, this characteristic time of interaction of the heat source with the workpiece can be very small. For example, in laser powder bed additive manufacturing processes like direct metal laser sintering (DMLS) and SLS (selective laser sintering), the diameter of the heat source can be 0.1 mm or smaller, and the scanning speed of the heat source can be 1000 mm/s or faster, and therefore the characteristic interaction time of the heat source with the workpiece can be much less than 1 ms and could be close to 100 microseconds.

With respect to the material response, for the aforementioned laser powder bed processes, the material response will be dominated by heat conduction. The characteristic time for heat conduction is given by the following equation:

$$t_{material\ response} = \frac{X^2}{4\alpha} \quad (2)$$

Where X is a characteristic length over which heat conduction occurs, and $\square$ is the thermal diffusivity of the material. For many metals, the thermal diffusivity is on the order of 10-8 m2/s. If we take the same characteristic distance, i.e. the beam diameter which is assumed to be 100 microns, then the characteristic time for the material response is on the order of 0.25 seconds. Therefore, it is seen that the faster characteristic time is 1000 to 10,000 times faster than the slower characteristic time. This means that the timescale over which heat input into the process is 100 to 10,000 faster than the timescale over which the material is able to dissipate this heat. In other words, the heat input characteristic time is significantly faster than the materials response time.

This is a universally observed phenomenon for rapid thermal processes such as laser welding, electron beam welding, and even many arc welding processes where the travel speed of the arc is high or the energy density of the arc is high. This is also a prevalent process condition for many additive manufacturing processes that are based on lasers and electron beams and involve the addition of material either through a sequentially layered and melted or sintered powder bed or the direct addition of material through wire fed by a mechanical wire feeder or powder being fed by a nozzle where the powder may by fluidized, carried, or otherwise entrained in an inert gas stream.

Embodiments of the present invention can measure these two very different process timescales associated with a manufacturing process where thermal energy is added rapidly by a scanning external heat source. Embodiments of the present invention can derive process features from these thermal data gathered on these two very different timescales.

For manufacturing processes that add heat and that achieve significant temperatures such that there are radiative emissions coming from the process, another mode of sensing is spectroscopy. The radiation that is thus emitted is both blackbody radiation as well as characteristic radiation. The blackbody radiation is a function of the temperature of the process and is governed by Planck's Equation:

$$I(v, T) = \frac{2hv^3}{c^2} \frac{1}{e^{\frac{hv}{kT}} - 1} \quad (3)$$

Where I is the intensity of radiation emitted per unit time per unit area normal to the emitting surface, T is the absolute temperature of the surface in degrees Kelvin, h is the Planck constant, k is the Boltzmann Constant, c is the Speed of Light, and $\square$ is the frequency of the radiation emitted. The relationship between the absolute temperature and the wavelength of the maximum emitted radiation is given by Wien's Displacement Law:

$$\lambda_{max} = \frac{b}{T} \qquad (4)$$

Where b is a constant.

In addition to the blackbody radiation which is a function of temperature, there are characteristic radiation peaks in the spectral data which are due to photons emitted as a result of specific electronic transitions between quantum states of atoms excited by multi-photon processes or by direct electron collisions. These are called characteristic because they are characteristic to a particular atom and ionization state(s). These will manifest in the spectral data as specific peaks at specific wavelengths. There will often be multiple peaks associated with various elements and electronic transitions, and as a result this spectral data can quickly get very complex.

Specifically with respect to additive manufacturing as performed by either laser or electron beam sintering of powders, the optical radiation is a by-product of the interaction between the beam and the powder bed. At lower energy fluences, where the fluence is defined as watts of incident energy absorbed per unit area, the powders may not melt completely and due to the fact that the powders have very poor thermal conductivity, the top surfaces of the powders can heat up and cause a larger amount of optical radiation even when there is no melting. At very high fluences where there is significant melting, the increased power can cause excessive liquid temperatures as well as excessive vaporization, thus leading to increased optical emissions. In the middle range of fluences which is neither too high nor too low, the optical emission can undergo a local minimum due to the fact that the energy is optimally coupled to the powder bed, i.e. there is not excessive surface heating due to poor thermal conductivity nor is there excessive liquid heating and vaporization.

If the integration times of the spectrometer as well as the incident beam time of the laser were absolutely identical and the spectrometer always saw optical emissions for a given fixed time when the laser was within the field of view of the spectrometer, and if the same chemical species were present in the vaporized plume in the same atomic percentages, then the absolute value of the intensity of the optical emission at a given characteristic spectral line could be used as an indicator of energy coupling to the powder bed. However the following intervening factors prevent the use of the absolute value of spectral peaks as a feature that could be used to gauge the extent of energy coupling between the incident energy beam and the powder bed during an additive manufacturing process:

The spectrometer will have a certain finite field of view over a certain region of the powder bed. Depending on the scan pattern of the laser or electron beam, the beam will intersect this fixed field of view for different periods of time. Thus, during a fixed shutter open time (also equal to the spectrometer integration time), the laser or electron beam will not intersect the spectrometer field of view in the same way or the same number of times. This will result in variations in the intensity signal The atomic concentration of species that are either excited neutral species or ionized and are giving off characteristic radiation will vary as a function of the power level. Also, in a multi-element, multi-component alloy, there could be several elements contributing to the spectral lines and several of these elements may have closely spaced lines, especially for transition metals found in most common engineering alloys that have complex electronic transition states and hence complex associated spectra. This complex variation of atomic species that are responsible for the characteristic emissions—both in terms of atomic composition and relative atomic percent—results in variations in the absolute value of the spectral intensity at any given wavelength which makes it difficult to utilize this absolute value as a feature.

As a result of these and possibly other intervening factors, it is desirable to select another feature that could allow the characteristic spectral data to be used as a discriminator to see when the energy coupling between the laser or electron beam and the powder bed may be optimal. The FFT—Fast Fourier Transform—of the spectral data will indicate where any given spectrum is undergoing more rapid change in value. When there is a greater atomic concentration of a given excited neutral or ionized species in the plume above the energy beam/powder bed interaction zone and these species are emitting characteristic radiation, it is expected that the corresponding spectral peaks will be sharper and will therefore have higher values of FFT intensity at a given inverse wavelength. Conversely, when the characteristic emissions are lower due to the fact that there are relatively fewer excited species due to a more optimal energy coupling, then the relative peak at a given wavelength will be broader and the background blackbody radiation will play a more dominant role in the spectral intensity at that given wavelength. Therefore the FFT intensity peak under such conditions at the same inverse wavelength would be lower than that observed otherwise. Therefore the FFT intensity at some intermediate inverse wavelength (which will depend on the alloy composition) can serve as an indicator of the relative coupling efficiency of the incident energy beam to the workpiece.

Embodiments of the present invention can utilize spectrometry data to determine relative energy coupling efficiency between an incident energy beam and a workpiece in an additive manufacturing process. Embodiments of the present invention can determine the relative coupling efficiency by utilizing the FFT—the Fast Fourier Transform— of the spectral data as a distinguishing feature that will allow such a classification of a local optimum in energy coupling efficiency. Embodiments of the present invention can utilize the FFT feature thus derived to determine a local minimum in this same FFT signal that indicates a condition in which the coupling between the energy source and the workpiece. In the case of an additive manufacturing process that utilizes a powder bed and a laser or electron beam to build up parts layer by layer. Embodiments of the present invention can utilize the FFT feature and more specifically a local minimum in the FFT feature to determine the conditions under which the energy coupling between the laser or electron beam and the powder bed is optimal.

MODES OF CARRYING OUT THE INVENTION, AND INDUSTRIAL APPLICABILITY

Figure 1:
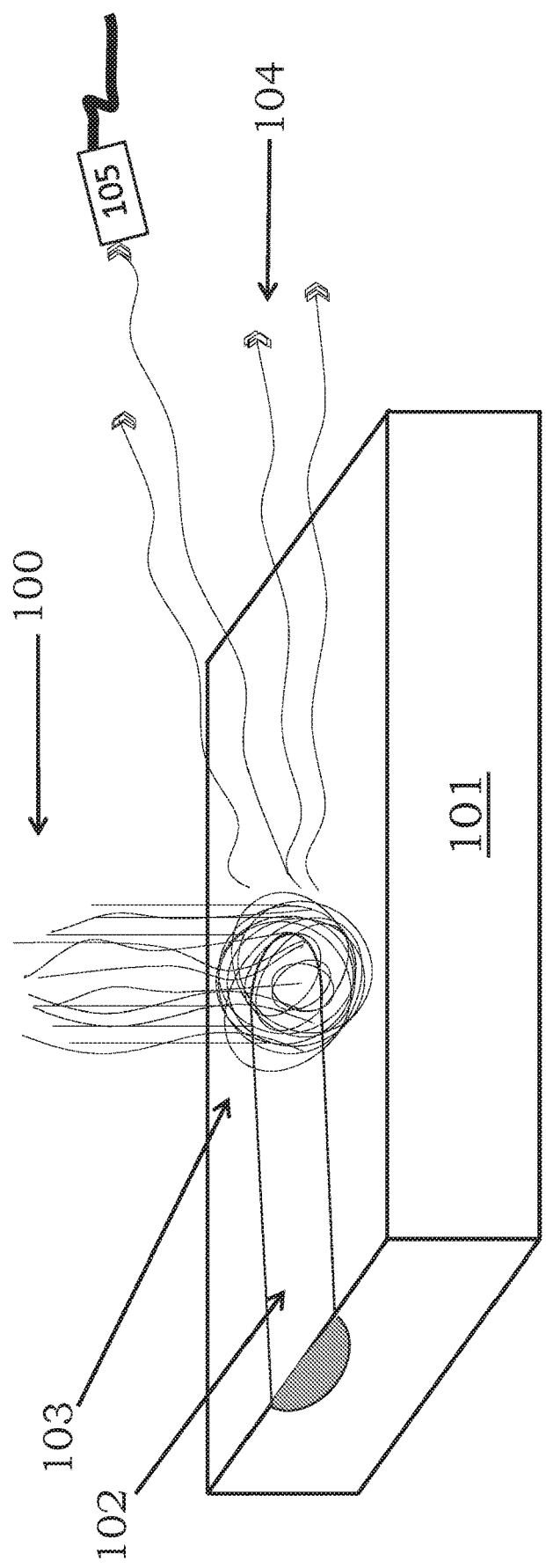
FIG. 1 is a schematic illustration of a heat source impinging upon a workpiece.

In FIG. 1, a heat source 100 is shown impinging upon a workpiece 101. There is a molten region 102 on the workpiece directly below the region of the workpiece 101 affected by the energy source 100. There also could be a region of ionized or vaporized material 103 which is above the molten region 102. Both the molten region 102 and the vaporized or ionized region 103 will emit optical radiation 104. This radiation is detected by an optical sensor 105. The sensor can be stationary with respect to the energy source, also known as an Eulerian reference frame, or it can be in the same reference frame as the moving energy source, also known as a Lagrangian reference frame.

Figure 2:
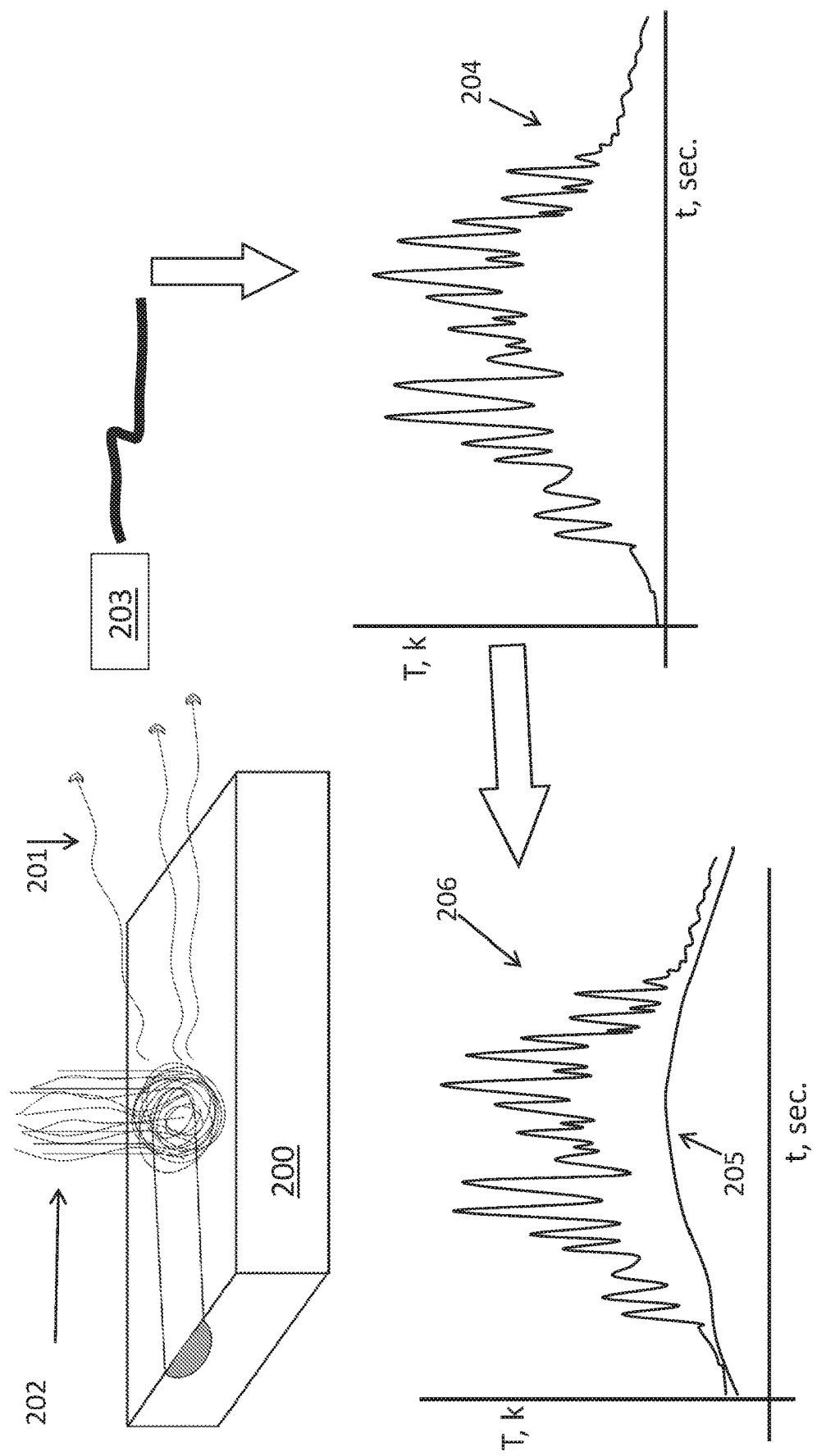
FIG. 2 is a schematic illustration of a workpiece giving off optical radiation due to heating by a heat source and the optical sensor is a non-contact pyrometer.

In FIG. 2, the workpiece 200 gives off optical radiation 201 due to heating by the heat source 202 and the optical sensor is a non-contact pyrometer 203. This pyrometer collects a thermal signal 204. It is assume that the size of the heat source 202 is smaller than the size of the field of view of the pyrometer. The thermal signal comprises two type of features: a slower moving signal 205 that is associated with the heat source 202 gradually coming into the field of the view of the pyrometer as well as representing the background temperature of the workpiece 200; and a faster moving signal 206 that represents individual high temperature excursions caused by the heat source 202 as it moves into and out of the field of view of the pyrometer.

Figure 3:
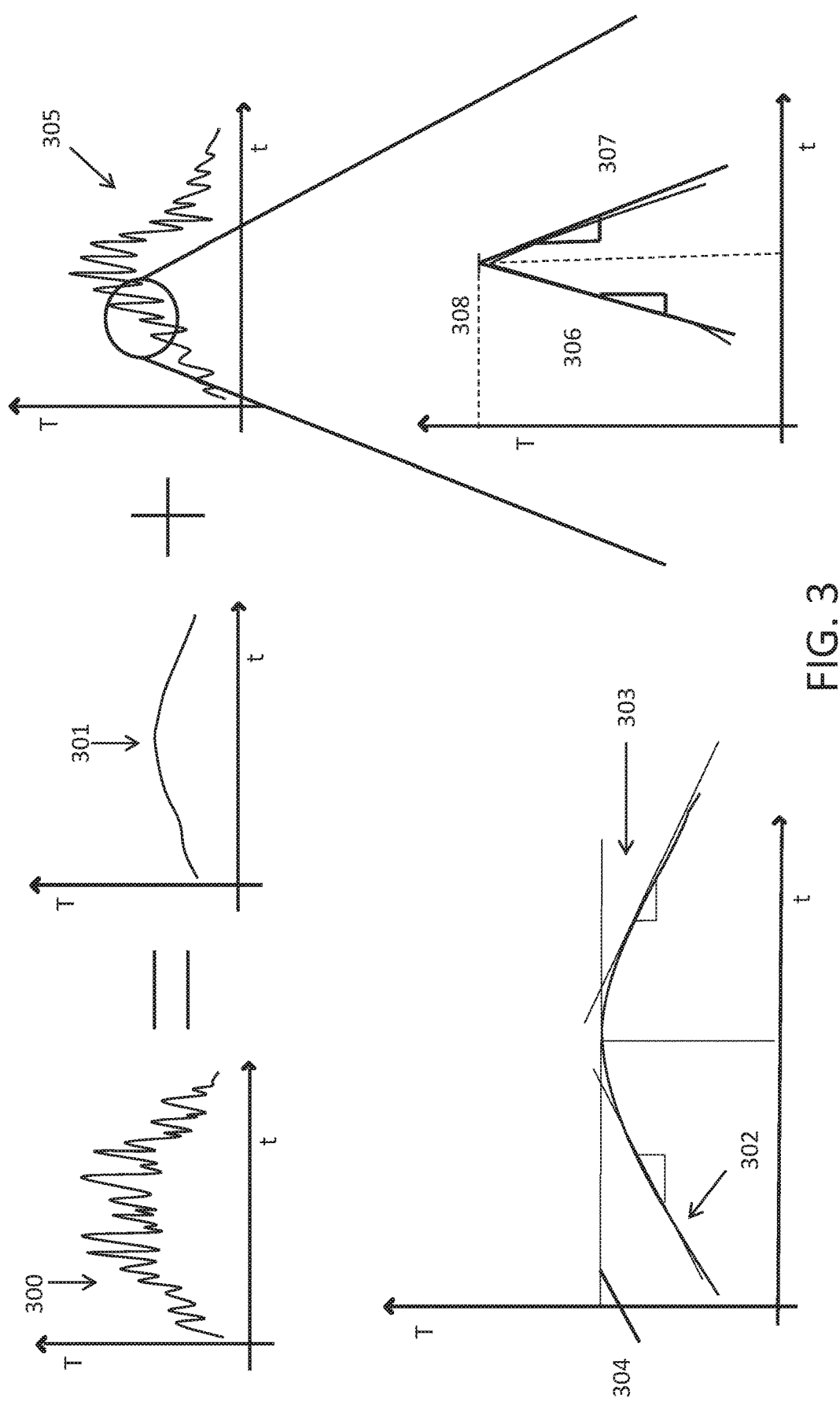
FIG. 3 is a schematic illustration of raw pyrometer signals, which are then transformed by extracting features therefrom.

In FIG. 3, the raw pyrometer signals 300 are then transformed by extracting features from this data. There are several types features that can be extracted. First, from the slower varying data 301 the heating rate 302 and cooling rate 303 as well as the peak background temperature 304 can be extracted. Secondly, from the faster varying data 305, the heating rate 306, the cooling rate 307 and the peak temperature 308 can be derived. The slower varying data features indicated by 302, 303, and 304 correspond to the material response, as it is largely dictated by the local thermal boundary conditions such as the thermal conductivity, heat sinking properties, etc. Additionally, the slower varying thermal data indicates the background temperature of the workpiece in between scan events from the moving heat source. This again is related to the material response as opposed to the thermal input from the process. The more rapidly varying data features indicated by 306, 307, and 307 are more representative of the process inputs and the energy inputs to the manufacturing process on account of the scanning energy source.

Figure 4:
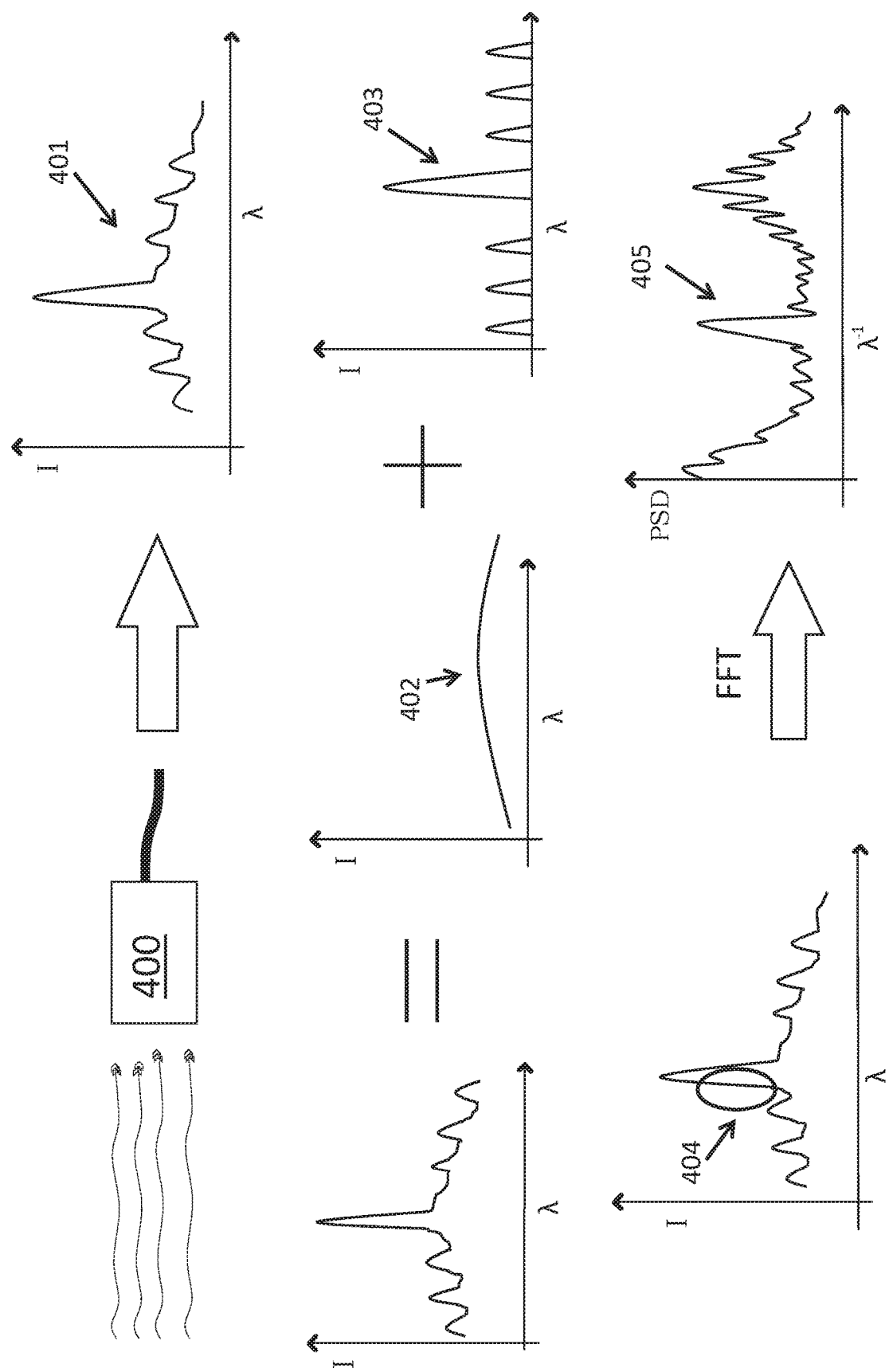
FIG. 4 is a schematic illustration of an optical sensor that is capturing the optical emissions from the radiation process, comprising a spectrometer where the raw spectrum shows integrated spectral intensity as a function of wavelength.

In FIG. 4, the optical sensor that is capturing the optical emissions from the radiation process is a spectrometer 400 which results in the raw spectrum 401 showing integrated spectral intensity as a function of wavelength. In general any spectrum will have both background blackbody radiation features 402 as well as characteristic radiation features 403. It is possible to extract features from raw spectrum by taking the FFT and examining the peak heights in the FFT at some intermediate values of the inverse wavelength. For example the region of more rapid change in the wavelength domain peak 404 can correspond to a local maximum in the FFT 405 in the inverse wavelength domain. The slower the rise of the wavelength domain peak 404 would then correspond to a lower value of the corresponding FFT peak 405. This particular example could happen for example when the wavelength domain peak is caused by evaporation of given chemical species. The lower this evaporation, the lower the spectral intensity and the slower the rise towards the spectral peak because of the nature of the Gaussian fit of the spectral peak. This for example could happen when the energy coupling to the workpiece is optimal in the sense that energy is being absorbed, there is a stable liquid melt pool, and there is sufficient superheat to overcome the latent heat of melting for new powders being sintered but not so much superheat so as to cause excessive vaporization.

Irrespective of how the features are derived, whether they are from the thermal sensor or the spectrometer, the classification scheme can be the same. First, the features associated with a baseline condition are identified as one set of data. Then the features from any given test case can be compared to the baseline condition as follows. First the features from the baseline case are averaged and a vector of the mean of these features M is created. The test vector X has the same dimensionality as the vector of feature means because it has the same number of features, which will be also called the degrees of freedom. Then a classification scheme as taught in this present invention involves the use of the Mahalanobis distance, which is simply given by:

$$MD^2 = [\overline{X} - \overline{M}]^T \cdot COV_X [\overline{X} - \overline{M}] \quad (5)$$

Where $COV_X$ is the covariance matrix of X. It can be shown that when the features are normally distributed, then the square of the MD distance will be Chi-Square distributed. The Chi Squared probability density distribution is given by:

$$f(x; k) = \begin{cases} \dfrac{x^{(k/2)-1} e^{-x/2}}{2^{k/2} \Gamma\left(\dfrac{k}{2}\right)}, & x \geq 0; \\ 0, & \text{otherwise.} \end{cases} \quad (6)$$

Where Γ is the Gamma Function and k is the number of degrees of freedom, which in this case is identical to the number of features. The critical value of the Chi-Squared distribution at a given confidence level and a given number of degrees of freedom can be calculated. This is a threshold value of the distribution above which a point could be considered as an outlier within the context of fitting the MD Distance t a Chi-Squared distribution. For example, at a 95% confidence level, or a critical p-value of 0.05, the corresponding table of critical values of the Chi-Squared distribution and therefore the MD distance squared as well are given by the following table:

| Degrees of Freedom (also the number of Features in the Feature Vector) | Critical Value of the Chi-Squared Distribution - also critical value of the square of the MD distance |
| --- | --- |
| 1 | 3.84 |
| 2 | 5.99 |
| 3 | 7.82 |
| 4 | 9.49 |

-continued

| Degrees of Freedom (also the number of Features in the Feature Vector) | Critical Value of the Chi-Squared Distribution - also critical value of the square of the MD distance |
|---|---|
| 5 | 11.07 |
| 6 | 12.59 |
| 7 | 14.07 |
| 8 | 15.51 |
| 9 | 16.92 |
| 10 | 18.31 |

The present invention provides a method of utilizing optical data through a variety of sensors as well as a variety of feature extraction techniques to enable the classification of nominal vs. off-nominal conditions found in a variety of manufacturing processes that involve the application of heat by a high energy or high temperature transient heat source.

The present invention has been described in the context of various example embodiments. It will be understood that the above description is merely illustrative of the applications of the principles of the present invention, the scope of which is to be determined by the claims viewed in light of the specification. Other variants and modifications of the invention will be apparent to those of skill in the art.

What is claimed is:

1. A system, comprising:
an energy beam;
an optical sensor configured to collect spectral data from a plume generated by a coupling between the energy beam and a workpiece during an additive manufacturing operation;
a processor configured to:
apply a fast fourier transfer function to the spectral data; and
determine a coupling efficiency of the energy beam incident to the workpiece based upon the transformed spectral data; and
a status indicator configured to communicate the results of the coupling efficiency at a given instant in time to a human machine interface.

2. The system as recited in claim 1, wherein the optical sensor is a spectrometer.

3. The system as recited in claim 1, wherein the processor is further configured to determine an atomic concentration of one or more excited neutral or ionized species in the plume based on the transformed spectral data.

4. The system as recited in claim 1, wherein the optical sensor is a multiple wavelength pyrometer.

5. The system as recited in claim 1, wherein the optical sensor is configured to measure optical emissions having wavelengths of between 200 and 1000 nanometers.

6. The system as recited in claim 1, wherein the status indication system is configured to record the results of the determined coupling efficiency.

7. The system as recited in claim 1, wherein the energy beam scans across a build plane during the additive manufacturing process and the optical sensor is stationary relative to the scanning energy beam.

8. The system as recited in claim 1, wherein determining the coupling efficiency of the energy beam incident to the workpiece comprises measuring peak heights of the transformed spectral data.

9. The system as recited in claim 1, wherein the energy beam is a laser.

10. The system as recited in claim 1, wherein the energy beam scans across a build plane during the additive manufacturing process and the optical sensor is in the same reference frame as the scanning energy beam.

11. An additive manufacturing method, comprising:
collecting spectral data emitted from a plume generated by a coupling between an energy beam and a workpiece during an additive manufacturing operation;
applying a fast fourier transfer function to the spectral data;
determining a coupling efficiency of the energy beam incident to the workpiece based upon the transformed spectral data; and
communicating the coupling efficiency at a given instant in time to a human-machine interface.

12. The additive manufacturing method as recited in claim 11, further comprising recording the results of the coupling efficiency at a sequential series of times during the additive manufacturing operation.

13. The additive manufacturing method as recited in claim 12, wherein the optimal coupling efficiency corresponds to the energy beam creating a stable liquid melt pool.

14. The additive manufacturing method as recited in claim 11, wherein the spectral data is collected by a multiple wavelength pyrometer.

15. The additive manufacturing method as recited in claim 11, wherein transformed spectral data indicative of the optimal coupling efficiency comprises spectral data with low characteristic emissions.

16. The additive manufacturing method as recited in claim 11, wherein determining the coupling efficiency of the energy beam incident to the workpiece comprises measuring peak heights of the transformed spectral data.

17. The additive manufacturing method as recited in claim 11, wherein determining the coupling efficiency comprises:
determining intensity vs wavelength of the transformed spectral data;
normalizing the spectral data by either the highest peak height or a suitable peak height elsewhere in the spectra should the highest peak height exhibit signal saturation prior to applying the fast fourier transform; and
determining an intermediate relative maximum of the transformed spectral data.

18. The additive manufacturing method as recited in claim 17, wherein the presence of a local minimum in a plot of intensity of the transformed spectral data as a function of incident power fluence as measured in power per unit area is used as an indicator of a more optimal coupling of incident energy to the workpiece.

19. The additive manufacturing method as recited in claim 11, wherein the energy source is a laser that scans in a pattern corresponding to a desired shape of the workpiece.

20. The additive manufacturing method as recited in claim 11, wherein communicating the coupling efficiency at a given instant in time to a human-machine interface is performed by a status indication system.

* * * * *